United States Patent
Hughes

(10) Patent No.: US 7,183,779 B2
(45) Date of Patent: Feb. 27, 2007

(54) SOIL PROBE DEVICE AND METHOD OF MAKING SAME

(75) Inventor: William C. Hughes, Woodstock, IL (US)

(73) Assignee: Spectrum Technologies, Inc., Plainfield, IL (US)

( * ) Notice: Subject to any disclaimer, the term of this patent is extended or adjusted under 35 U.S.C. 154(b) by 0 days.

(21) Appl. No.: 11/025,009

(22) Filed: Dec. 28, 2004

(65) Prior Publication Data

US 2006/0139037 A1    Jun. 29, 2006

(51) Int. Cl.
*G01R 27/08*    (2006.01)
*G01R 27/26*    (2006.01)

(52) U.S. Cl. .................. 324/696; 324/688; 324/664

(58) Field of Classification Search ............... 324/696, 324/694, 693, 691, 649, 600, 437, 445, 446, 324/715, 724, 72.5, 751, 752, 754, 757, 758, 324/690, 149, 664, 688
See application file for complete search history.

(56) References Cited

U.S. PATENT DOCUMENTS

| | | |
|---|---|---|
| 3,934,477 A | 1/1976 | Thettu |
| 3,936,729 A | 2/1976 | Winslow, Jr. |
| 3,965,973 A | 6/1976 | Thettu et al. |
| 3,968,428 A | 7/1976 | Numoto |
| 3,982,177 A | 9/1976 | Walker et al. |
| 4,020,417 A | 4/1977 | Brehob et al. |
| 4,160,946 A | 7/1979 | Frigato |
| 4,197,866 A | 4/1980 | Neal |
| 4,219,776 A | 8/1980 | Arulanandan |
| 4,408,481 A | 10/1983 | Sidey |
| 4,416,553 A | 11/1983 | Huebscher |
| 4,419,023 A | 12/1983 | Hager, Jr. |
| 4,441,827 A | 4/1984 | Coderre |
| 4,445,788 A | 5/1984 | Twersky et al. |
| 4,498,547 A | 2/1985 | Herkness, II |
| 4,575,706 A | 3/1986 | Heidman, Jr. |
| 4,583,432 A * | 4/1986 | Bricker ................. 82/1.11 |
| 4,585,996 A | 4/1986 | Luce |
| 4,594,899 A | 6/1986 | Henke et al. |

(Continued)

OTHER PUBLICATIONS

*Soil Solution Electrical Conductivity Measurements Using Different Dielectric Techniques*, Soil Sci. Soc. Am. J. 67:1071-1078, Y. Hamed, M. Persson and R. Berndtsson (2003) (8 pages).

(Continued)

*Primary Examiner*—Andrew H. Hirshfeld
*Assistant Examiner*—Hoai-An D. Nguyen
(74) *Attorney, Agent, or Firm*—Bell, Boyd & Lloyd LLC

(57) ABSTRACT

A device for measuring one or more different properties of soil or a soil-related substance is provided. The device includes a probe that is inserted into the soil or soil-related substance. The probe includes a tip. The tip is electrically insulative and defines apertures. Electrodes are fitted into the apertures. The tip and electrodes are machined together to have a desired shape that is suitable for insertion into a sample. A printed circuit board ("PCB") is located inside the probe. The electrodes are soldered directly to the PCB in one embodiment. A temperature sensing element is also located in the tip, near the electrodes, and is connected electrically to the PCB.

20 Claims, 4 Drawing Sheets

U.S. PATENT DOCUMENTS

| | | | |
|---|---|---|---|
| 4,626,786 A | 12/1986 | Bodecker et al. | |
| 4,692,695 A | 9/1987 | Poduje | |
| 4,791,413 A | 12/1988 | Lyczek | |
| 4,796,654 A | 1/1989 | Simpson | |
| 4,801,865 A | 1/1989 | Miller et al. | |
| 4,802,953 A | 2/1989 | Hoeksema et al. | |
| 4,806,153 A * | 2/1989 | Sakai et al. | 73/152.52 |
| 4,841,543 A | 6/1989 | Dittmar et al. | |
| 4,852,802 A * | 8/1989 | Iggulden et al. | 239/64 |
| 4,909,070 A | 3/1990 | Smith | |
| 4,929,885 A | 5/1990 | Dishman | |
| 4,956,535 A | 9/1990 | Buelt et al. | |
| 5,015,988 A | 5/1991 | Fletcher | |
| 5,044,756 A | 9/1991 | Gaultney et al. | |
| 5,100,259 A | 3/1992 | Buelt et al. | |
| 5,179,347 A | 1/1993 | Hawkins | |
| 5,186,263 A | 2/1993 | Kejr et al. | |
| 5,209,129 A | 5/1993 | Jaselskis et al. | |
| 5,339,694 A | 8/1994 | Looney et al. | |
| 5,369,365 A | 11/1994 | Waitman | |
| 5,408,893 A | 4/1995 | McLeroy | |
| 5,411,103 A | 5/1995 | Werner | |
| 5,428,296 A | 6/1995 | Champagne et al. | |
| 5,435,399 A | 7/1995 | Peterson et al. | |
| 5,445,178 A | 8/1995 | Feuer | |
| 5,474,140 A | 12/1995 | Stevens | |
| 5,494,376 A | 2/1996 | Farrar et al. | |
| 5,495,170 A | 2/1996 | Feeney et al. | |
| 5,499,631 A | 3/1996 | Weiland | |
| 5,575,260 A | 11/1996 | Trost et al. | |
| 5,591,902 A | 1/1997 | Castagner | |
| 5,659,251 A | 8/1997 | Wakamatsu | |
| 5,663,649 A * | 9/1997 | Topp et al. | 324/643 |
| 5,673,637 A | 10/1997 | Colburn, Jr. et al. | |
| 5,749,521 A | 5/1998 | Lattery | |
| 5,777,242 A | 7/1998 | Zuidberg et al. | |
| 5,793,214 A | 8/1998 | Wakamatsu | |
| 5,795,064 A | 8/1998 | Mathis | |
| 5,801,537 A * | 9/1998 | Siddiqui et al. | 324/643 |
| 5,841,282 A | 11/1998 | Christy et al. | |
| 5,847,568 A | 12/1998 | Stashkiw et al. | |
| 5,859,536 A * | 1/1999 | Stockton | 324/664 |
| 5,874,672 A * | 2/1999 | Gerardi et al. | 73/170.26 |
| 5,879,107 A | 3/1999 | Kiest et al. | |
| 5,887,491 A | 3/1999 | Monson et al. | |
| 5,924,369 A | 7/1999 | Hatcher | |
| 5,931,236 A | 8/1999 | Mahlum et al. | |
| 5,933,015 A | 8/1999 | Siddiqui et al. | |
| 5,936,243 A | 8/1999 | Gibson et al. | |
| 5,945,830 A | 8/1999 | Magowan et al. | |
| 5,975,799 A | 11/1999 | Carrigan et al. | |
| 5,992,213 A | 11/1999 | Tartre | |
| 6,013,169 A | 1/2000 | Okubo et al. | |
| 6,018,909 A | 2/2000 | Potts | |
| 6,020,747 A | 2/2000 | Bahns et al. | |
| 6,058,776 A | 5/2000 | Algers et al. | |
| 6,081,110 A | 6/2000 | Moore et al. | |
| 6,110,288 A | 8/2000 | Penelon et al. | |
| 6,138,590 A | 10/2000 | Colburn, Jr. | |
| 6,145,600 A | 11/2000 | Dickinson | |
| 6,182,586 B1 | 2/2001 | Hunt et al. | |
| 6,208,940 B1 | 3/2001 | Kram et al. | |
| 6,215,317 B1 | 4/2001 | Siddiqui et al. | |
| 6,232,786 B1 | 5/2001 | Barnett | |
| 6,236,941 B1 | 5/2001 | Kram et al. | |
| 6,240,558 B1 | 6/2001 | Makris et al. | |
| 6,265,883 B1 | 7/2001 | Clark | |
| 6,289,714 B1 | 9/2001 | Tartre | |
| 6,326,790 B1 | 12/2001 | Ott et al. | |
| 6,352,002 B1 | 3/2002 | Weijer | |
| 6,356,830 B1 | 3/2002 | Adamchuck et al. | |
| 6,360,829 B1 | 3/2002 | Naber et al. | |
| 6,366,106 B1 | 4/2002 | Kimori et al. | |
| 6,401,742 B1 | 6/2002 | Cramer et al. | |
| 6,431,006 B1 | 8/2002 | Henke et al. | |
| 6,452,396 B2 | 9/2002 | Ott et al. | |
| 6,452,397 B2 | 9/2002 | Ott et al. | |
| 6,456,079 B2 | 9/2002 | Ott et al. | |
| 6,467,951 B1 | 10/2002 | Ghoshal | |
| 6,481,939 B1 | 11/2002 | Gillespie et al. | |
| 6,484,652 B1 | 11/2002 | Colburn, Jr. | |
| 6,494,961 B2 | 12/2002 | Simpson | |
| 6,509,440 B1 | 1/2003 | Sakane et al. | |
| 6,515,220 B1 | 2/2003 | Carpenter, Jr. | |
| 6,529,007 B2 | 3/2003 | Ott et al. | |
| 6,549,852 B2 | 4/2003 | Hanson | |
| 6,559,659 B2 | 5/2003 | Cuming | |
| 6,560,550 B2 | 5/2003 | Omar | |
| 6,571,605 B2 | 6/2003 | Johnson | |
| 6,581,531 B2 | 6/2003 | Sawers et al. | |
| 6,603,315 B2 | 8/2003 | Dahms | |
| 6,618,673 B2 * | 9/2003 | Zur | 702/2 |
| 6,630,947 B1 | 10/2003 | Lieberman et al. | |
| 6,647,799 B1 | 11/2003 | Raper et al. | |
| 6,657,443 B2 | 12/2003 | Anderson | |
| 6,683,464 B2 | 1/2004 | Park et al. | |
| 6,745,128 B2 | 6/2004 | Hanson | |
| 6,750,450 B2 | 6/2004 | Mukasa et al. | |
| 6,766,865 B1 | 7/2004 | Dagel et al. | |
| 6,767,747 B1 | 7/2004 | Bischoff et al. | |
| 6,784,666 B2 | 8/2004 | Andreasen | |
| 6,819,120 B2 | 11/2004 | Tam | |
| 6,831,470 B2 | 12/2004 | Xie et al. | |
| 2004/0066181 A1* | 4/2004 | Thies | 324/72.5 |

OTHER PUBLICATIONS

*A Pore Water Conductivity Sensor*, Soil Sci. Soc. Am. J. 64:1922-1925, M.A. Hilhorst (2000) (4 pages).

*Spectrum Your Field Measurement Resource*, Spectrum Technologies, inc. www.specmeters.com, Oct. 25, 2004 (19 pages).

*SigmaProbe type ECl Salinity and nutrient monitoring, Soil Water and Plant Measurement*, pp. 11, 12.

*SigmaProbe type ECl*, Sigma-P probe leaflet sowacs.com/feature/deltat/sigmaprobe.html, Dec. 13, 2004 (2 pages).

*Dual-purpose Conductivity Meter for Direct Measurement in Soil and Liquids*, Spectrum Technologies, Inc. (3 pages).

*Bodenmessgaräte Bodenuntersuchungen Zubehör*, Stelzner, Jan. 2004 (48 pages).

*Spectrum Your Field Measurement Resource*, Spectrum Technologies, Inc. catalogue, Spring 2004 (32 pages).

\* cited by examiner

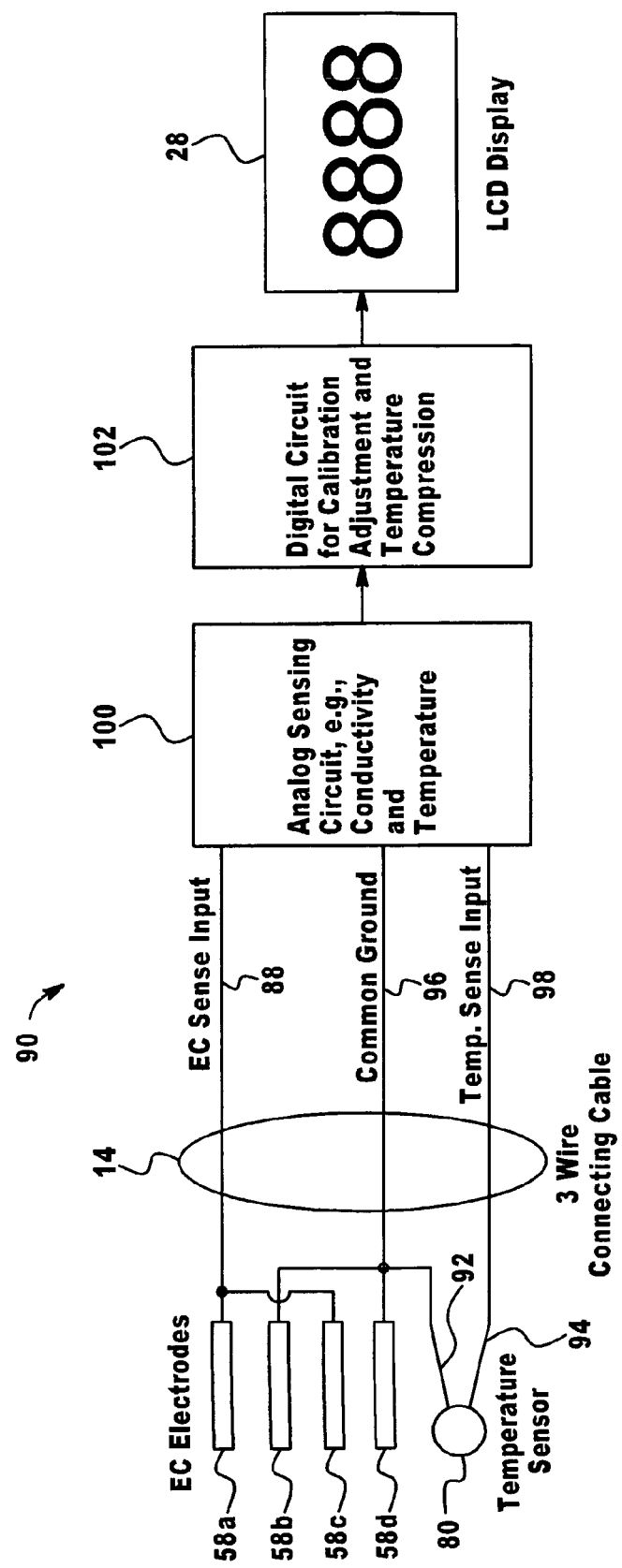

SOIL PROBE DEVICE AND METHOD OF MAKING SAME

BACKGROUND OF THE INVENTION

The present invention relates to soil science and hydrology and more particularly to the measurement of soil properties.

Plants require an adequate supply of soluble nutrients to grow well. Also, land reclamation and leachate management require the build-up of dissolved salts and pollutants over large areas to be monitored. In both applications, the solute concentration and water content in soil are the two primary control factors. Indeed, solute concentrations and water content in media such as soil, sand and soil-less media can measure and control many soil conditions, such as irrigation and fertilization conditions, surface runoff, erosion and salinity.

Regarding proper fertilization, the lack of nutrients and overfertilization can both cause problems. It is the concentration of the plant available nutrients dissolved in water, rather than the measurement of total nutrients, that is the pertinent concentration, e.g., to determine if fertilization is required (nutrient level too low) or if fertilization should be stopped (nutrient level too high).

Regarding salinity, salinity refers to the presence of major dissolved inorganic solutes or nutritive salts in aqueous samples. The inorganic solutes or nutritive salts include, for example, $Mg^+$, $Ca^{2+}$, $K^+$, $Cl-$, $SO_4^{2-}$, $HCO_3^-$, and $CO_3^{2-}$. Salinity is the total concentration of such salts. For agricultural applications, it is imperative to ensure that the salinity level is not too high. For example, most crops are tolerant of a salinity range between 0 and 100 mS/m and intolerant of a salinity range between above 400 mS/m. Irrigation water should also be checked to ensure that its salinity is not too high.

The conductivity of water in soil (referred to herein as pore water) indicates the presence or lack of the above-listed nutritive salts. Pore water conductivity has been measured in the past by suctioning the pore water from the soil or by creating a saturated soil paste and measuring the conductivity of such paste. Those methods are time consuming and error prone. Another technique for estimating pore conductivity is a dielectric technique known as time domain reflectometry ("TDR"). The TDR technique is relatively expensive and difficult to handle for example in a greenhouse in which multiple samples of different pottings of soil need to be taken.

A need therefore exists to provide a soil analysis measurement and control device that can handle each of the above applications, which is relatively easy to use and transport, which can take relatively quick readings, which can take multiple readings in series to monitor different soil portions, and which is relatively inexpensive and rugged.

SUMMARY OF THE INVENTION

The present invention includes a soil probe device and method of manufacturing a soil probe. The device includes a probe, circuitry and a meter. The probe and meter in an embodiment measure conductivity, such as the conductivity of soil samples (greenhouse, potted plants, bedding plants, containers, compost, cultural soil mixtures, agricultural samples, land reclamation samples, etc.), irrigation water, fertilization solutions and any other soil, sand or soil-less media (referred to collectively herein as a soil media or sample).

The conductivity reading can be indicative of the level of nutritive salts (such as those discussed above) existing within the soil media or sample. The device is portable and can take multiple readings in series of different samples or readings of the same sample at different times (e.g., before and after fertilization to establish the effectiveness of such fertilization and to ensure the resulting soil is not too saline and potentially damaging to the roots of the plant potted in the sample).

The device provides conductivity measurements of irrigation water and fertilizer mixes, ensures saline values are within acceptable ranges and that a correct fertilizer concentration and strength is applied. Further, the device ensures that conductivity readings of solutes diffused in land reclamation soil are below a specified level.

To operate the device, the user inserts the probe into the sample. The probe enables an electrical signal indicative of the conductivity of the soil media to be generated and processed via circuitry located in the device. In an embodiment, the device also provides temperature compensation for the ultimate conductivity reading. The temperature compensation may require a few seconds for the temperature reading to stabilize. Once the reading has stabilized, the device provides a steady and accurate reading to the user.

The electrical signal indicative of the conductivity of the soil media may be used to provide the user with one or more different types of information about the sample. In one embodiment, the signal is converted to display, digitally, a temperature-compensated conductivity in mS/cm or mS/m. In another embodiment, the signal is converted to display, digitally, a temperature-compensated activity of the ions dissolved in the soil. Such ion activity is shown in units of grams per liter. The temperature compensation is performed using a separate signal generated via a temperature sensing element.

In a further embodiment, the signal is indicative of the pore water concentration. That signal is then converted to display, digitally, a moisture content of the soil. The moisture content reading can also be temperature compensated via a separate temperature signal. In still a further alternative embodiment, the signal is used in combination with a signal from a load cell or force sensor, wherein the two signals are converted and combined to display, digitally, a level of compaction of the soil.

One component of the device is a probe. The present invention provides a probe having multiple advantages. The probe includes multiple electrodes. The electrodes press-fit through apertures defined in a tip of the probe. The apertures are spaced radially around the tip (which is conical in one embodiment) and at a distance from a distal end of the tip that is approximately equal. Such configuration enables each of the electrodes to be located near the end of the tip. Locating the electrodes near the end of the tip yields a probe that does not need to be inserted very far into the sample to provide an accurate reading. The probe is therefore well-suited for many applications having shallow samples, such as trays of seedlings used commonly by greenhouses and other growers.

In one embodiment, the tip is made of a machinable, insulative material, such as a machinable plastic. One suitable material is Delrin™ manufactured by Dupont™. The electrodes press-fit into the insulative material are collectively lathe-cut, milled or otherwise formed to have a desired finished shape. In one implementation the tip and electrodes are formed together to have a conical shape that aids the user when inserting the probe into a soil sample. The electrodes are cut to be smooth with the side of the conical insulative tip, forming elliptically shaped electrode ends.

The insulative material, such as Delrin™, has a relatively low coefficient of friction and low moisture absorption properties. The low moisture absorption and insulative properties of the tip material enable stable and repeatable signals to be generated. The low coefficient of friction reduces wear on the tip caused potentially by friction and forces due to insertion into the samples. Likewise, the electrode material is a relatively hard and corrosion resistant material in one embodiment, such as stainless steel or titanium. Also, the electrode material can be solderable for direct connection to a printed circuit board or other apparatus.

The tip of the probe is connected to a probe housing, which can be metal or hard plastic tubing. A small printed circuit board ("PCB") is placed between the electrodes, inside the housing. In one embodiment, the electrodes are soldered directly to traces placed on the PCB. For example, the probe may include four total electrodes, forming two electrode pairs. One of the electrodes of each pair is a signal electrode and the other a ground electrode. In one implementation, one pair of electrodes is soldered to traces located on a first side of the PCB, while a second pair of electrodes is soldered to traces located on a second side of the PCB.

A temperature sensing element is also connected electrically to the PCB. In one implementation, the temperature sensing element is a thermistor. The thermistor includes a sensing head that is embedded into the tip. A pair of wires extends from the thermistor head and connects electrically to traces on the PCB. The head is located adjacent to the electrodes and at a same depth as the exposed electrode ends. Such placement helps to ensure that the temperature the thermistor measures represents the temperature of the soil adjacent to the electrodes.

The probe housing is attached to the tip assembly, which includes the insulative tip, the electrodes, the PCB and temperature sensing element. The housing in an embodiment is filled with epoxy. The epoxy helps to seal out moisture and contaminants, which could effect the results of the device. The epoxy also provides a strain relief at the joints between the wires and the PCB, yielding an overall more robust device.

In an embodiment three wires extend from the PCB, through and out the housing of the probe, through a flexible and waterproof conduit, and to a meter. The meter houses the electronic circuitry and visual readout and in an embodiment is waterproof. The meter also includes user inputs, such as membrane switches. The input switches can include a mode switch, which enables the same display area to display different units selectively, such as conductivity units, temperature units, ion activity units, moisture units, compaction units, etc.

It is therefore an advantage of the present invention to provide an improved soil media analysis device.

It is another advantage of the present invention to provide an improved probe for a soil media analysis device.

It is a further advantage of the present invention to provide a probe for a soil media analysis device that may be inserted into shallow soil media samples.

It is yet another advantage of the present invention to provide a soil media analysis device that is rugged, water proof and non-corrosive.

It is still another advantage of the present invention to provide a soil media analysis device that is readily portable.

It is yet a further advantage of the present invention to provide a soil media analysis device that can display different useful soil media properties selectively.

Additional features and advantages of the present invention are described in, and will be apparent from, the following Detailed Description of the Invention and the figures.

BRIEF DESCRIPTION OF THE FIGURES

FIG. 7 is a schematic view of one embodiment of an electrical layout for the soil media analysis device of the present invention.

DETAILED DESCRIPTION OF THE INVENTION

Figure 1:
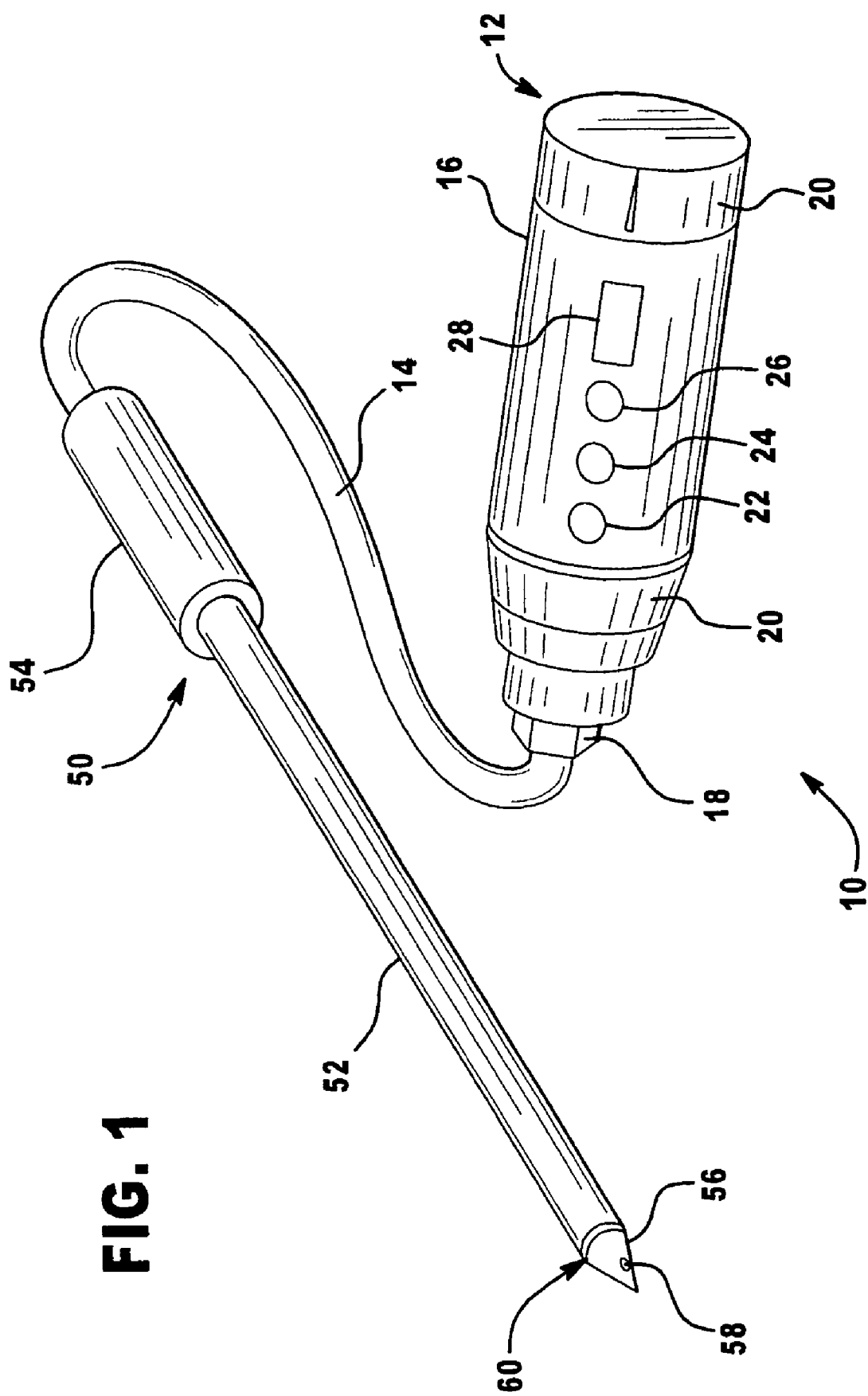
FIG. 1 is a perspective view of one embodiment of a soil media analysis device of the present invention.

Referring now to the drawings and in particular FIG. 1, one embodiment of a soil media analysis device 10 is illustrated. Device 10 includes a meter 12 and a probe 50, which is attached to meter 12 via conduit 14. Meter 12 houses electronic circuitry and a display or readout discussed in more detail below.

Probe 50 is robust, waterproof and readily inserted into many different soil media applications, including shallow soil samples common in greenhouses and other growers. The soil media herein above can be any one or more of a variety of different types of earthen materials. For example, the soil media or sample can be a soil sample (for a greenhouse, potted plants, bedding plants, containers, compost, cultural soil mixtures, agricultural samples, land reclamation samples, etc), irrigation water, fertilization solutions and any other type of soil, sand or soil-less material. The Probe 50 and Meter 12 are not limited however to soil media applications and instead can be used to measure any liquid or liquidous substance.

The reading displayed on meter 12 can be displayed in any of a plurality of units, such as units of conductivity (e.g., mS/cm or mS/m,) units of soil ion activity (e.g., grams per liter), units of moisture content (e.g., percent moisture) or units of compaction (e.g., a cone index or pressure units). Device 10 can be provided with one or more sensors and various circuitry to measure and display any one or more of the above-mentioned soil media properties. Probe 50 may be used, alone or in combination with a second (integral or separate) sensor, such as a load cell, for any such property or combination of properties.

The output of probe 50 may be manipulated to be used with different types of devices. In one embodiment, device 10 includes circuitry that measures and reads out electro-conductivity or soil moisture. In another embodiment, device 10 includes circuitry for both electro-conductivity and soil moisture, so that device 10 can measures and reads out both properties. Soil moisture affects soil solute concentration, which is measured by measuring the conductivity of the soil. A meter that can measure both soil conductivity and soil moisture is therefore advantageous.

Probe 50 can be combined with an additional (integral or separate) load cell to provide a combination electro-conductivity/soil compaction meter. Such combination electro-conductivity/soil compaction meter can also include circuitry that measures and reads out soil moisture. In any of the above-described embodiments, the circuitry can be configured to display units of ion activity (e.g., grams of salt ions per liter of soil). A customer may prefer one set of units, e.g., mS/cm or grams/liter. A reading of 0.05 grams of salt ions per liter of salt may for example indicate an insufficient soil activity, while a reading above 1.5 may indicate a toxic activity. In essence, soil conductivity and soil ion activity are a measure of the same thing, e.g., soil effectiveness.

As seen in FIG. 1, meter 12 includes a body 16. Body 16 is coupled to connector 18 and end caps 20 via O-rings or other type of sealing mechanism that produces a waterproof encasement of the electronics and circuitry housed within body 16 of meter 12.

Meter 12 also includes a number of user inputs, such as an on/off input 22, a mode input 24 and a hold input 26. On/off input 22 turns device 10 on and off. Mode input 24 toggles meter 12 between the different types of readouts discussed herein. It should also be appreciated that in addition to the various soil media properties that can be measured as described herein, mode input 24 can also toggle meter 12 so that the soil media temperature is displayed. Hold input 26 enables the user to freeze the display of a particular reading for a particular time, and then to touch hold input 26 again to unlock the reading and display the present output. In an embodiment, inputs 22, 24 and 26 are membrane switches provided under a waterproof seal.

Meter 12 also includes a readout 28, which can be a digital readout. In an embodiment, display or readout 28 is a liquid crystal display or a light emitting diode display, which displays a desired amount of significant digits, such as three significant digits, as well as the appropriate units, such as mS/cm (or mS/m) for conductivity, grams per liter for soil ion activity, percent $H_2O$ for moisture content or a cone index or pressure reading for a soil compaction readout. In an embodiment, a clear and waterproof membrane is placed over a part or all of body 16 between end caps 20 to seal the inputs 22, 24 and 26 and readout 28.

Body 16, end caps 20, connector 18 and conduit 14 in an embodiment are plastic, rubber or otherwise made of a light, strong and water resistant or non-absorbent material. Conduit 14 as illustrated is flexible so that probe 50 may be inserted into a soil media sample at one angle, while the user observes meter 12 at a different angle. The flexible nature of conduit 14 also enables probe 50 and meter 12 to be stored and transported readily. Conduit 14 is sized appropriately to hold the number and gauge of wires extending from probe 50 to meter 12.

As seen in FIG. 1, probe 50 includes a housing 52, a protective Hand Grip 54 and a tip assembly 60. Tip assembly 60 includes an insulative tip 56 embedded with sensing electrodes 58. Tip assembly 60 is discussed in more detail below in connection with FIGS. 2 to 5.

Housing 52 in an embodiment is a tube, such as a metal or hard plastic tube. In one implementation, housing 52 employs a stainless steel tube having a ⅜ inch outside diameter. In one preferred embodiment, housing 52 is waterproof, corrosion resistant and non-absorbent. Hand Grip 54 fits over the proximal end of housing 52 and seals the interface between housing 52 and conduit 14. Hand Grip 54 is made of a hard plastic or rubber material in various embodiments. Hand Grip 54 is likewise waterproof and non-absorbent.

Referring now to FIGS. 1 to 5, various views of tip assembly 60 are illustrated. As seen in FIG. 1, tip assembly 60 is fastened and sealed to the distal end of housing 52. One method for assembling probe 50 is to prepare tip assembly 60 as seen in FIGS. 2 to 5 and then fasten same to housing 52 of probe 50 as seen in FIG. 1.

Tip assembly 60 includes insulative tip 56 and electrodes 58a to 58d (referred to herein collectively as electrodes 58 or generally as electrode 58) inserted into the tip. Tip 56 includes an extension 62 and a midsection 64. Extension 62 has a smaller outer diameter than does midsection 64. Tip 56 also includes a pointed end 66, which is made suitable for insertion into soil, sand or other earthen material, which may be relatively dense or heavily compacted.

Tip 56 is inserted into housing 52 until midsection 64 abuts the distal end of housing 52. Reduced diameter extension 62 is sized to press-fit or fit snuggly within the inner diameter of housing 52. While a generally cylindrical probe is illustrated, probe 50 may alternatively be square shaped, rectangular shaped or otherwise have any suitable desired cross-sectional shape. A glue or sealant may be applied between extension 62 and housing 52, so that tip 56 is further sealed to housing 52 when the assembly is made.

Tip 56 in an embodiment is made from an electrically insulative and non-absorbent material, which also has a relative low coefficient of friction. One material suitable for tip 56 is Delrin™ made by Dupont™. The material of tip 56, such as Delrin™, is in one preferred embodiment relatively hard and able to withstand the rigors of repeated insertion into the soil media sample.

Tip 56 may be preformed with the apertures through which electrodes 58 are inserted. In another embodiment, the apertures are drilled into tip 56 after the tip is formed. To that end, the material of tip 56 is machineable in one embodiment. In an embodiment, tip 56 is formed initially as a blank having a cylindrical shape (not illustrated) rather than the displayed conical shape. The apertures for electrodes 58 are drilled or formed longitudinally through the cylindrical blank for tip 56. In an embodiment, the diameters of the apertures are slightly less than the outer diameters of electrodes 58, so that electrodes 58 can be pressed-fitted into the apertures. If needed, a suitable glue or adhesive is also applied to adhere electrodes 58 within the apertures of tip 56.

After securing electrodes 58 within the cylindrical blank of tip 56, tip 56 is lathe-cut, milled or otherwise formed into its final desired e.g., conical shape. In the illustrated embodiment, the final desired shape of tip 56 is conical. Alternatively, tip 56 may include any suitable shape, such as a blunt pointed end, elliptical end, round end, diamond end or other end suitable for insertion into a soil media sample. The blank for tip 56 may therefore be square, rectangular or have any other suitable cross-sectional shape.

During the lathe-cutting, milling or other forming process, the portion of electrodes 58 that would otherwise extend out of the final shape of tip 56 are cut or milled off. The resulting ends of electrodes 58 of assembly 60 have the same contour and radius as does insulative tip 56. That is, the electrodes and insulative tip 56 combine to produce an overall smooth and desired shape. In an embodiment, tip 56 and cut electrodes 58 are sand-blasted or bead-blasted, which improves the tip's surface characteristics and provides for more stable readings.

As illustrated, electrodes 58a to 58d at their distal ends have an elliptical shape due to the conical shape of tip 56. The distal ends of electrodes 58 are each located at approximately the same distance from the furthest distal end or point 66 of tip 56. This configuration enables tip 56 to have a relatively low profile, which facilitates insertion of probe 50 into shallow samples, such as small seedling pottings common in greenhouses and other plant growers.

In an embodiment, electrodes 58a to 58d are spaced apart an equal radial distance around tip 56. Electrodes 58 are also connected electrically so that any two adjacent electrodes are connected to opposite pluralities (i.e., to a signal or ground plurality). The resulting sensing area of tip 56 therefore spreads the measurement of electrical current around the circumference of tip 56.

In an embodiment, a voltage source (not illustrated) is located in meter 12 and applies a voltage across pairs of the electrodes 58. The voltage source can be one or more batteries, such as three 1.5 volt batteries (totaling 4.5 volts). The voltage source causes a quantity of current to pass through each of the electrode pairs and the media to be measured, which completes a circuit between the electrode tips. In one embodiment, meter 12 includes circuitry to convert the direct current provided by the voltage source to an alternating current that flows through electrodes 58. The alternating current avoids potential polarization problems that direct current may cause at the electrodes. The amount of current passing through the electrodes is indicative of, e.g., the bulk conductivity of the soil media. Circuitry within meter 12 measures and converts the current into a conductivity or other property, which is then readout on display 28.

Assembly 60 further includes a printed circuit board ("PCB") 70. PCB 70 is illustrated in more detail in connection with FIGS. 6A and 6B. As seen on PCB 70 of FIGS. 6A and 6B, PCB 70 includes a plurality of traces and mounting pads. In particular, mounting pads 72, 74, 76, 82, 84 and 86 are provided. In an embodiment, electrodes 58a to 58d are each soldered directly to one of the pads 72, 74, 82, and 84 of PCB 70 (electrode 58a to pad 74, electrode 58b to pad 72, electrode 58c to pad 82 and electrode 58d to pad 84). To that end, electrodes 58 are made of a non-corrosive and solderable conductive material, such as stainless steel. Alternatively, electrodes 58 can be titanium or other suitable conductive material and may be connected to PCB 70 via a wire or clip.

Soldering electrodes to PCB 70 directly allows for structurally reliable connections and reduces the size of assembly 60 and ultimately the size of the outer diameter of housing 52. As illustrated, half, e.g., two, of the electrodes are soldered to one side of PCB 70, while the other half (e.g., the other two) of the electrodes are soldered to the opposite side of PCB 70. The thickness of PCB 70 is configured such that the PCB fits snuggly between electrode pairs 58a/58b and 58c/58d to facilitate the direct soldering of those electrodes. The electrode/PCB configuration yields an overall assembly 60 that is relatively rugged, reliably connected and compactly configured.

Figure 5:
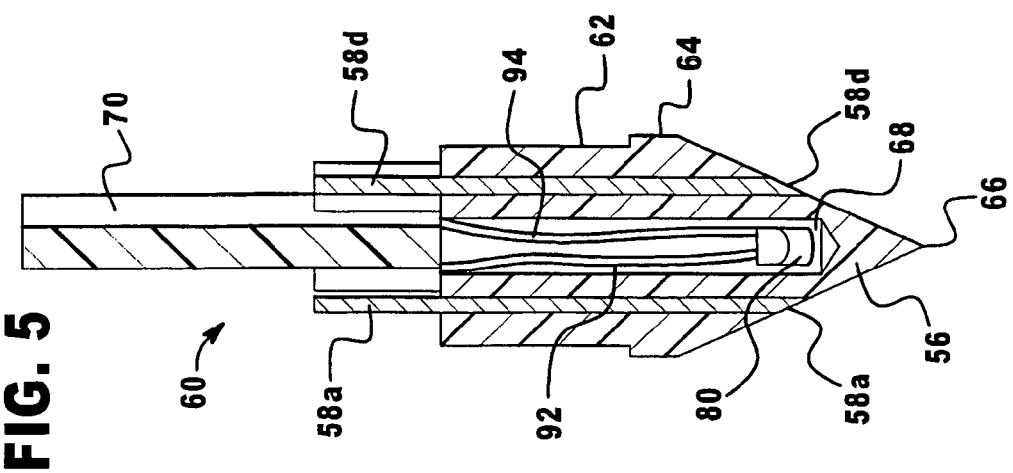
FIG. 5 is a sectioned side elevation view of the assembled tip taken along line V—V of in FIG. 3.
Figure 3:
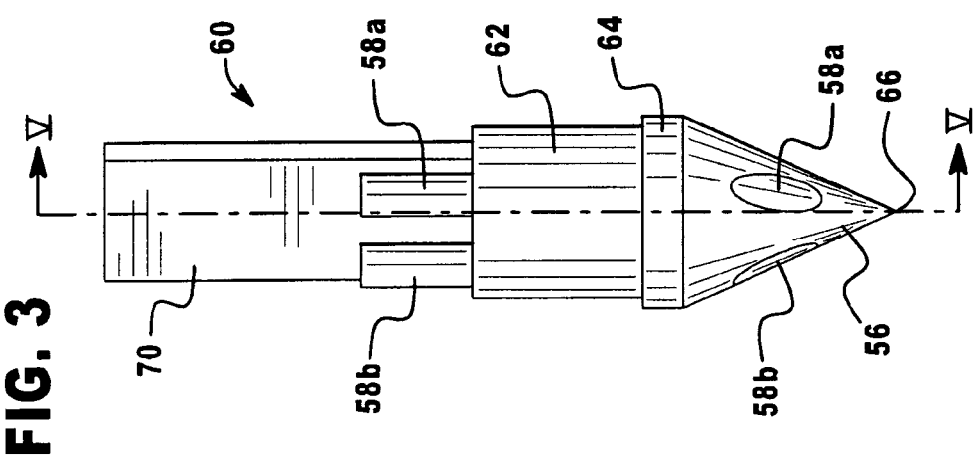
FIG. 3 is a side elevation view of the assembled tip shown in FIG. 2.
Figure 2:
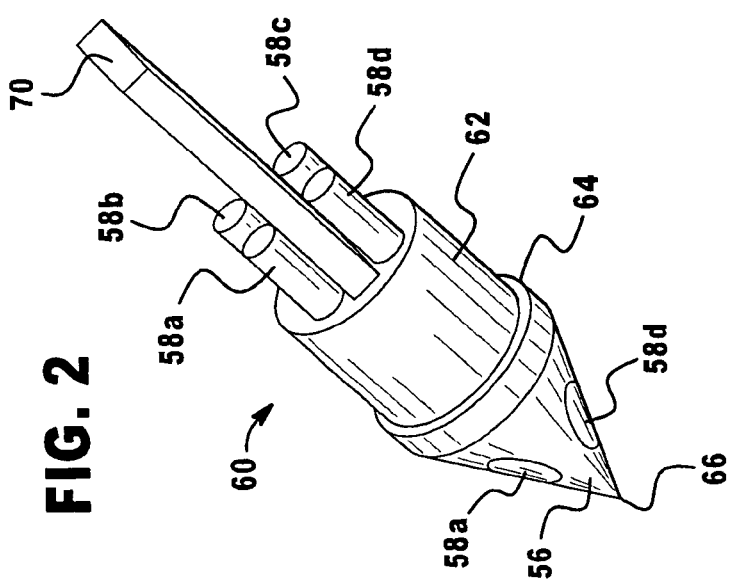
FIG. 2 is a perspective view of one embodiment of an assembled tip of the probe of the present invention.

Tip assembly 60 further includes a temperature element 80 shown in the sectioned view of FIG. 5. Sensing element 80 in an embodiment is a thermistor, such as a PTC or NTC type thermistor. In general, a thermistor is a type of resister used to measure temperature changes, relying on the change in its resistance with changing temperature. In an embodiment, thermistor or sensing element 80 is powered by the same power supply that provides power to electrodes 58a to 58d. Other types of temperature sensing elements, such as a resistance temperature detector ("RTD") or a thermocouple, may be used alternatively.

As seen in FIG. 5, tip 56 defines an internal cavity or lumen 68 into which a head of thermistor or temperature sensing element 80 is placed. The head of thermistor or temperature sensing element 80 is held fixed in one embodiment via its attachment to PCB 70. If needed, an epoxy or other device may be used to help secure the head of element 80 in place, so that the head resides at a position that is spaced apart from pointed end 66 of tip 56 approximately equally with the distal ends of electrodes 58. That is, the depth at which the sensing head of element 58 is fixed matches or is in-line with, at least substantially, the location of exposed areas of electrodes 58. Such configuration helps to ensure that the temperature measured represents the soil temperature at the electrodes 58.

The measurement of temperature enables temperature compensation of the electrode conductivity measurement, for example, to be made so that display 28 of meter 12 reads out a conductivity (or other temperature sensitive property) that has been compensated for temperature. The temperature sensing element 80 also enables the temperature of the soil media to be shown on display 28.

Temperature sensing element 80 includes a pair of leads 92 and 94 that extend through aperture 68 defined by tip 56 and connect to PCB 70. Viewing FIGS. 6A and 6B, leads 92 and 94 of temperature sensing element 80 connect respectively to center pads 86 and 76 of PCB 70. Thus, PCB 70 provides electrical connections for each of the electrodes 58 and temperature sensing element 80. In an embodiment, leads 92 and 94 are soldered directly to pads 86 and 76, respectively, in a similar manner as the electrodes are soldered to pads 72, 74, 82 and 84.

Figure 6B:
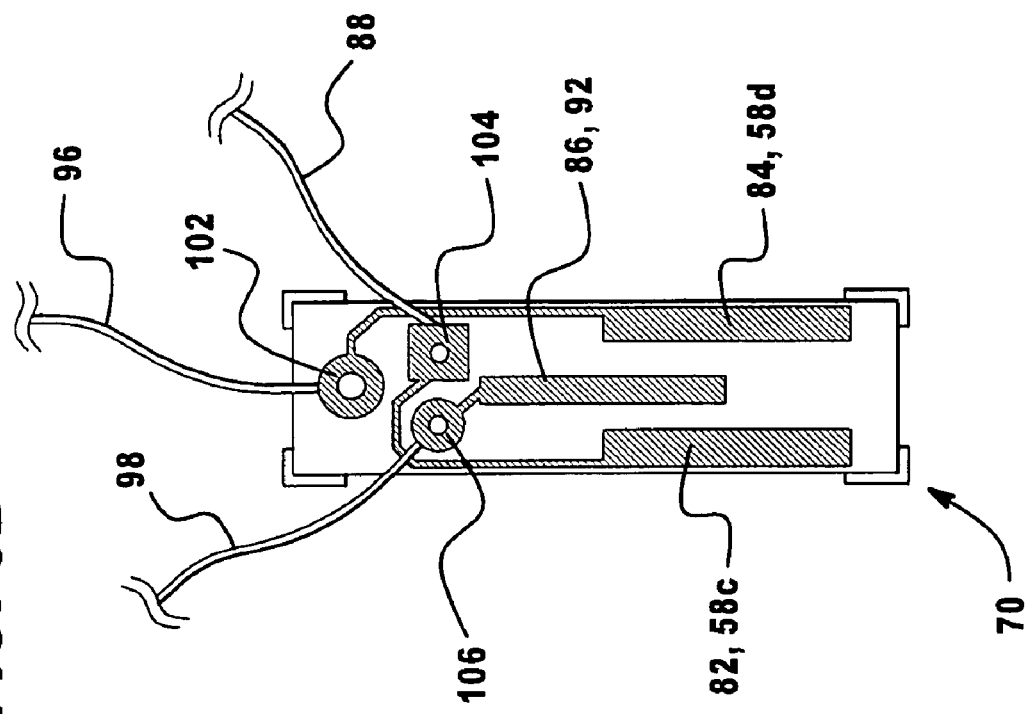
FIG. 6B is top view of a bottom surface of the printed circuit board shown FIG. 6A.
Figure 6A:
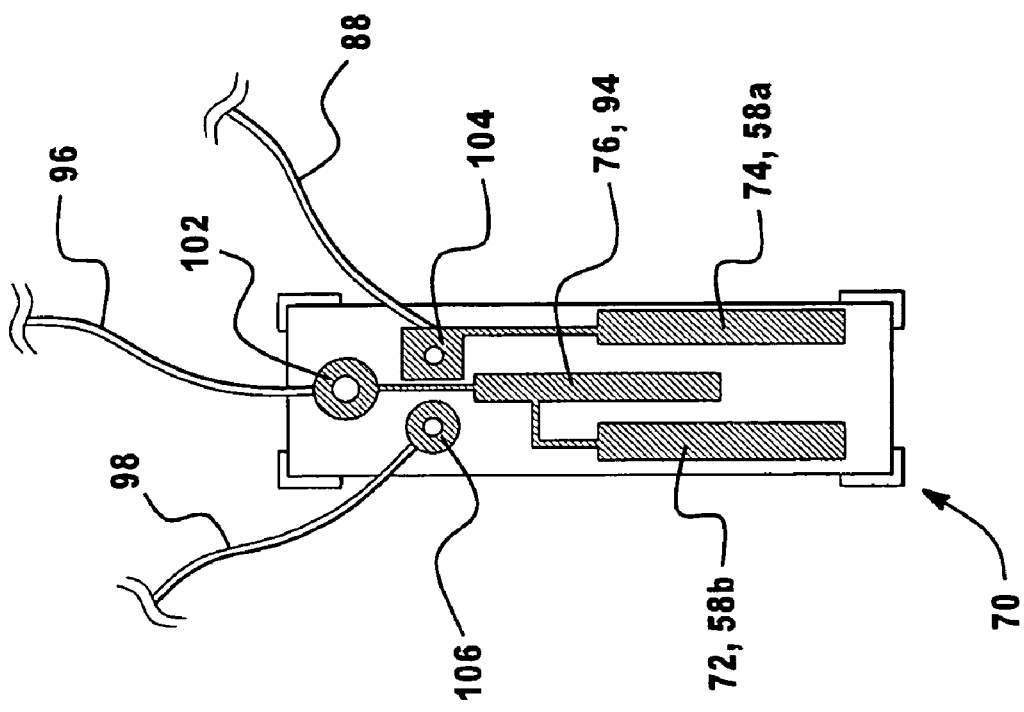
FIG. 6A is top view of a top surface of one embodiment of a printed circuit board shown in the assemblies of FIGS. 2 to 4.

Referring now to FIGS. 6A, 6B and 7, a further description of the electrical operation of soil media sensing device 10 is illustrated. FIG. 7 shows an electrical schematic 90 for device 10. Certain apparatuses described above are shown again in schematic 90. For example, schematic 90 illustrates schematically electrodes 58a to 58d. Schematic 90 illustrates that electrodes 58a and 58c are signal electrodes, outputting a signal indicative of, e.g., electro-conductivity along a signal line 88 leading to circuitry 100 within meter 12. Electrodes 58b and 58d are ground electrodes, which link with lead 92 of temperature sensing element 80 to a common ground line 96, which extends to circuitry 100 within meter 12.

Schematic 90 also shows temperature sensing element 80. Temperature sensor lead 94 of element 80 connects electrically to a temperature signal input line 98, which extends to circuitry 100 within meter 12. The three lines or wires 88, 96 and 98 are housed within housing 52, conduit 14 (shown schematically in FIG. 7) and meter 12. Housing 52 in an embodiment is filled with and epoxy that seals moisture out of housing 52 and also relieves a strain that a pulling of wires 88, 96 and 98 may apply to the connection of such wires to PCB 70.

In FIGS. 6A and 6B, ground line 96 is shown connected to a pad 102 located on both sides of PCB 70. Signal line 88 is connected to a pad 104 located on both sides of PCB 70. Temperature sensing line 98 is connected to pad 106 located on both sides of PCB 70.

Figure 4:
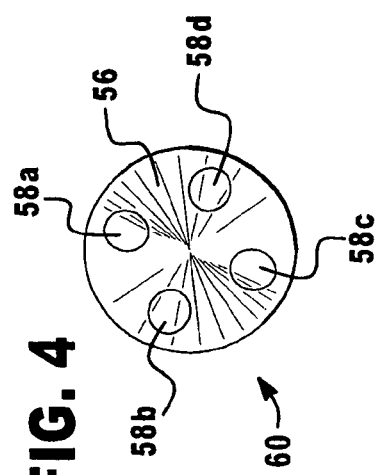
FIG. 4 is a front elevation view of the assembled tip shown in FIG. 2.

As seen in FIG. 4, signal electrodes 58a and 58c in tip 56 are spaced apart from one another and separated by ground electrodes 58b and 58d, which are in turn spaced apart from one another and separated by the signal electrodes. As such, the sensory measurement for whatever property is being measured and displayed is distributed around the conical radius of tip 56. As seen in FIGS. 6A and 6B, signal electrodes 58a and 58c are isolated on opposite sides of PCB 70. Ground electrodes 58b and 58d are isolated on opposite sides of PCB 70.

The number of electrodes 58 provided is a function of the size of tip 56 and the diameter of the electrode material (e.g., about 0.078 inch or 2.0 mm). As few as two electrodes may be provided, one signal and one ground electrode. Alternatively, multiple pairs of terminals may be provided, e.g., three pairs (six total electrodes 58) or four pairs (eight total electrodes 58) may be provided. In one preferred embodiment, the signal and ground electrodes are alternated regardless of how many pairs of electrodes 58 are provided.

As seen in FIG. 7, three wires 88, 96 and 98 pass through conduit 14 and conduct electrically with analog sensing circuitry 100, for example, circuitry relating conductivity and temperature. Circuitry 100 generates an analog signal, which is sent to Circuitry 102. Circuitry 102 converts the analog signal to a digital signal for calibration adjustment and temperature compensation. The digital signal is then displayed on digital readout 28. Circuitry 100 and 102 is specific to the various types of soil media property being sensed. That is, there is different circuitry for determining moisture content, ion activity of the soil and percent compaction.

One suitable meter 12 may be purchased from Oakton Instruments, Vernon Hills, Ill., Model #WD-35661-43. Probe 50 is operable with such meter to display conductivity in mS/cm and temperature in degrees Celsius. It is contemplated to provide an alternative meter, which includes circuitry that converts the current measurement into a readout of soil ion activity in grams of salt ions per liter. It is also contemplated to provide an alternative meter, which includes circuitry that converts the current measurement into a readout of percent moisture of the soil media. The soil moisture circuitry could be provided in combination with the electro-conductivity or ion activity. The resulting device 10 could then be (i) toggled to display either electro-conductivity/ion activity, percent moisture (either of which can be temperature compensated via a separate temperature signal) or soil temperature; or (ii) configured to display any combination of electro-conductivity/ion activity, percent moisture, (either of which can be temperature compensated) and soil temperature simultaneously.

In a further alternative embodiment, a load cell or other force sensor is provided in combination with probe 50. The load cell measures the cone resistance or insertion force for probe 50, which is indicative of the level of compaction of the soil. The force sensor may be integral with probe 50, e.g., provided in the same or in-line housing with tip 56, electrodes 58, PCB 70 and other apparatus of probe 50 described above. Or, the force sensor may be provided separately from probe 50, e.g., wherein conduit 14 is split with one branch extending to probe 50 and the other branch extending to the force sensor. In such case, meter 12 includes circuitry for both probe 50 and the force sensor.

The resulting device 10 could then be (i) toggled to display either electro-conductivity/ion activity (which can be temperature compensated via a separate temperature signal), percent compaction or soil temperature; or (ii) configured to display any combination of electro-conductivity/ion activity (which can be temperature compensated) percent compaction and soil temperature simultaneously. Percent moisture circuitry could also be provided so that the multi-probe device also reads out percent moisture (which can be temperature compensated) selectively or simultaneously.

In any of the above-described alternative embodiments, the circuitry within meter 12 can accept the inputs from wires 88, 96 and 98 extending from probe 50. It should therefore be appreciated therefore that probe 50 is adaptable to be used with many different types of meters housing different types of circuitry and/or different combinations of circuitry.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A probe for a soil media measuring device, the probe comprising:
   a housing, the housing having a receiving end;
   a tip assembly configured to mount in the receiving end, the tip assembly including:
   a tip, the tip having a first end distal to the housing, wherein the tip assembly and the housing are separately formed and configured to be inserted within the soil media;
   a plurality of electrodes disposed in the tip at locations spaced at least substantially equally from the first end of the tip and at least substantially equally around the tip, the electrodes enabling a signal indicative of a property of the soil media to be generated with the device;
   a temperature sensing element that enables the device to provide temperature compensation; and
   wherein the temperature sensing element is disposed within an aperture formed in the tip and is spaced apart at least substantially equally with the electrodes from the end of the tip.

2. The probe of claim 1, wherein the tip includes at least one characteristic selected from the group consisting of being: (i) conically shaped, (ii) electrically insulative, (iii) of a machinable material, and (iv) of a material having a relatively low coefficient of friction.

3. The probe of claim 1, which includes a plurality of electrode pairs, one electrode of each pair being a ground electrode and one electrode of each pair being a signal electrode.

4. The probe of claim 3, wherein the ground and signal electrodes are spaced apart alternatingly about the tip.

5. The probe of claim 1, wherein the electrodes are made of a material having at least one quality selected from the group consisting of being solderable and being relatively non-corrosive.

6. The probe of claim 1, wherein the signal is indicative of a conductivity of the soil media.

7. The probe of claim 1, wherein the soil media is of at least one type selected from the group consisting of potting soil, bedding soil, cultural soil, compost, a fertilizer, a fertilization mixture, irrigation water, land reclamation soil and sand.

8. The probe of claim 1, wherein the temperature sensing element is coupled to a printed circuit board, and the electrodes are placed in electrical communication with traces on the printed circuit board.

9. The probe of claim 8, wherein the electrodes are coupled directly to the traces.

10. The probe of claim 8, wherein at least one of the traces is located on a first side of the printed circuit board and at least one of the traces is located on a second side of the printed circuit board.

11. The probe of claim 1, which is combined with a force sensor.

12. A probe for a soil media measuring device, the probe comprising:
   a housing;
   a tip assembly, the tip assembly configured to be carried by the housing, the tip assembly configured to include:
   a tip having a tapered end, wherein the tip assembly and the housing are separately formed and configured to be inserted within the soil media;
   a plurality of electrodes disposed within the tip, each of the plurality of radially arrayed substantially equally around the tapered end;
   a temperature sensing element that enables the device to provide temperature compensation;
   wherein the temperature sensing element is disposed within an aperture formed in the tip and is spaced apart at least substantially equally with the electrodes from the end of the tip; and
   a printed circuit board ("PCB") placed within the housing, the PCB including conductive traces, the electrodes placed in electrical communication with the traces.

13. The probe of claim 12, wherein the temperature sensing element is connected electrically to the PCB.

14. The probe of claim 12, wherein the housing is at least filled partially with an epoxy.

15. A soil media device comprising:
   a meter;
   electronic circuitry coupled operably with the meter; and
   a probe, the probe including:
   a housing having a first end in electrical communication with the meter and a second end disposed distal to the meter;
   a tip located at the second end of the housing, the housing and the tip separately formed and configured for insertion within the soil media;
   a plurality of electrodes secured to the tip at locations spaced at least substantially equally from an end of the tip, the electrodes enabling a signal indicative of a property of the soil media to be generated with the circuitry;
   a temperature sensing element that enables the device to provide temperature compensation; and
   wherein the temperature sensing element is disposed within an aperture formed in the tip and is spaced apart at least substantially equally with the electrodes from the end of the tip.

16. The soil media device of claim 15, wherein the meter displays units indicating a soil media property selected from the group consisting of conductivity and temperature.

17. The soil media device of claim 15, wherein the soil media is of at least one type selected from the group consisting of potting soil, bedding soil, cultural soil, compost, a fertilizer, a fertilization mixture, irrigation water, land reclamation soil and sand.

18. A method of manufacturing a probe for a soil media measuring device, the method comprising:
   providing a housing having a receiving end;
   providing a tip assembly configured to mount in the receiving end;
   providing a tip having a first end distal to the housing, wherein the tip assembly and the housing are separately formed and configured to be inserted within the soil media;
   forming a plurality of electrodes within the tip at locations spaced at least substantially equally from the first end of the tip and at least substantially equally around the tip, and configuring the electrodes to provide a signal indicative of a property of the soil media;
   forming an aperture within the tip; and
   inserting a temperature sensing element that enables the device to provide temperature compensation, wherein the temperature sensing element is disposed within the aperture and is spaced apart at least substantially equally with the electrodes from the end of the tip.

19. The method of claim 17, wherein forming the plurality of electrodes include machining the desired shape of the tip with the plurality of electrode disposed therein.

20. The method of claim 18, wherein machining includes lathe-cutting an insulative material and the plurality of electrodes.

* * * * *